United States Patent [19]

Mathis

[11] Patent Number: 5,795,064
[45] Date of Patent: Aug. 18, 1998

[54] METHOD FOR DETERMINING THERMAL PROPERTIES OF A SAMPLE

[75] Inventor: Nancy Mathis, Fredericton, Canada

[73] Assignee: Mathis Instruments Ltd., Fredericton, Canada

[21] Appl. No.: 536,454

[22] Filed: Sep. 29, 1995

[51] Int. Cl.$^6$ .................................................. G01N 25/18
[52] U.S. Cl. ............................................................. 374/44
[58] Field of Search ........................................ 374/44, 43

[56] References Cited

U.S. PATENT DOCUMENTS

| | | | |
|---|---|---|---|
| 3,263,485 | 8/1966 | Mahmoodi | 374/44 |
| 3,971,246 | 7/1976 | Sumikama et al. | 374/44 |
| 4,332,157 | 6/1982 | Zemel et al. | 374/44 |
| 4,364,676 | 12/1982 | Oja et al. | 374/44 |
| 4,575,260 | 3/1986 | Young | 374/44 |
| 4,842,418 | 6/1989 | Conti | 374/139 |
| 4,859,078 | 8/1989 | Bowman et al. | 374/44 |
| 4,995,731 | 2/1991 | Hori et al. | 374/44 |
| 5,112,136 | 5/1992 | Sakuma et al. | 374/44 |
| 5,165,794 | 11/1992 | Ortiz | 374/44 |
| 5,237,523 | 8/1993 | Bonne et al. | 374/44 |
| 5,297,868 | 3/1994 | Graebner | 374/44 |
| 5,452,601 | 9/1995 | Hori et al. | 374/44 |

FOREIGN PATENT DOCUMENTS

| | | | |
|---|---|---|---|
| 3835895 | 7/1989 | Germany | 374/44 |
| 0161140 | 6/1989 | Japan | 374/44 |
| 2003085 | 11/1993 | Russian Federation | 374/44 |
| 0823999 | 4/1981 | U.S.S.R. | 374/44 |
| 1206667 | 1/1986 | U.S.S.R. | 374/44 |
| 1749802 | 7/1992 | U.S.S.R. | 374/44 |

*Primary Examiner*—Diego F. F. Gutierrez
*Attorney, Agent, or Firm*—Paul Sharpe Marks & Clerk

[57] ABSTRACT

A method of measuring thermal conductivity of a sample in both a machine direction and a transverse direction. The method is carried out with a probe having a electroconductive member in each of the above-mentioned directions. Upon application of a current to the probe, fluctuations in the voltage are received as a result of contact with the sample. This information is then used to generate a thermal conductivity ratio.

5 Claims, 6 Drawing Sheets

METHOD FOR DETERMINING THERMAL PROPERTIES OF A SAMPLE

FIELD OF THE INVENTION

The present invention relates to a method for determining thermal conductivity and more particularly, the present invention relates to non-intrusive method for determining an anisotropic ratio for a given material.

BACKGROUND OF THE INVENTION

The quantitative evaluation of strength of materials is critical in engineering and construction. The strength of a material determines if it can be used for the desired application. Safety, durability, and ultimately, the end-users satisfaction depends on strength of a material. The current standard method of determining strength is to conduct a destructive test in which a precisely machined sample is stretched to a breaking or failure point.

A non-destructive means of indirectly testing strength of material is currently known in several forms. Infrared, dichroism and birefringence are optical methods that are non-intrusive and substantially non-destructive. Both of these methods have been correlated to strength of polymeric materials at low orientation indicated by low draw ratio. Although useful, once complete crystallinity has occurred in the polymeric material, the above-mentioned methods no longer predict accurately the strength of material.

In terms of thermal conductivity, this measure indicates the ability of a material to transfer heat. Polymeric materials have the ability to be oriented by extrusion or alternate methods of working. Once oriented, these materials conduct heat preferentially in the direction of orientation, this being due to the alignment in the molecular backbone of the polymer and it is generally known that heat is conducted more readily along the covalent bonds rather than intermolecularly. The orientation dependency exhibited by such materials is referred to as anisotropy. Various methods have been proposed in the prior art to obtain thermal conductivity data, one example of which is the thermocouple system. In this arrangement, thermal conductivity in polymers would be measured by inserting a hot wire/thermocouple into a sample to be tested in the molten state. Once the sample has set, the wire can be heated and the interfacial temperature rise monitored. Although useful, one of the major drawbacks associated with this method is that it is an intrusive process and requires a significant time investment in order to generate data.

Thermal conductivity in solids has been measured as a bulk isotropic property by comparative methods. Heated plates sandwiching a sample and thermocouples are used to measure heat flow through a sample. This method requires long test times as it is necessary for the system to reach steady state. The device described herein is not hindered by the sample thickness because it measures the temperature rise at the heated surface. One of the key drawbacks of the heated plate method is that two tests have to be conducted, one for each orientation in order to calculate an anisotropic ratio. Another drawback of the method is the time needed to prepare the samples to the necessary size specifications. The device described herein advantageously requires no sample preparation apart from ensuring a flat surface.

In U.S. Pat. No. 4,859,078, issued to Bowman et al., Aug. 22, 1989, there is disclosed an apparatus for non-intrusive measurement for thermal properties. The apparatus provides two heating and temperature sensors with one sensor adapted for positioning in thermal communication with the medium to be tested and a second sensor in thermal communication with the first sensor. Both of these sensors are heated or cooled to prevent net heat flow between them. This permits ease in determining the heat flow between the first sensor and the medium which measurements allow determination of the thermal conductivity among other thermal properties. Although a useful arrangement, the system provided for in this reference does not provide information for a plurality of directions in the sample. This information is required in order to generate an anisotropic ratio.

Sakuma et al., in U.S. Pat. No. 5,112,136, issued May 12, 1992, provides a method of and apparatus for measuring thermal conductivity. The apparatus is an intrusive apparatus and further relies on the use of a reference material in order to generate thermal conductivity data.

Other apparatus for measuring thermal conductivity in the art include those arrangements in U.S. Pat. No. 5,297,868 issued Mar. 29, 1994 to Graebner, U.S. Pat. No. 4,364,676, issued Dec. 21, 1982, to Oja et al., U.S. Pat. No. 4,995,731, issued Feb. 26, 1991, to Hori et al., U.S. Pat. No. 4,575,260, issued Mar. 11, 1986 to Young, U.S. Pat. No. 4,842,418, issued Jun. 27, 1989 to Conti and U.S. Pat. No. 5,165,794, issued Nov. 24, 1992 to Ortiz.

In view of what has been previously proposed in the prior art, there is a distinct need for a method of determining thermal conductivity which is capable of generating data for use in formulating a thermal conductivity anisotropic ratio. In addition, a need exists for a method which is non-invasive and non-destructive to the sample being tested. The present invention is directed to satisfying these needs.

SUMMARY OF THE INVENTION

One object of the present invention is to provide an improved method for determining thermal properties of a sample having anisotropic and isotropic properties.

Another object of the present invention is to provide a method of measuring thermal conductivity of a sample in both a machine direction and a transverse direction, comprising the steps of:

providing a measuring device having at least one electroconductive member in a transverse direction and at least one electroconductive member in a machine direction;

applying a current through at least one member of each of the electroconductive members in each direction;

determining an amount of voltage received by the sample for both the transverse direction and the machine direction; and generating a thermal conductivity ratio from detected voltage fluctuations for the machine direction and the transverse direction.

Advantageously, one embodiment of the present invention permits measurement of thermal conductivity in both a transverse direction and a machine direction. This information can be then compiled and a thermal conductivity anisotropic ratio generated. This is additionally advantageous since the apparatus is a non-intrusive apparatus and does not result in the destruction of a sample being tested. This is in marked contrast to the arrangements provided for in the prior art which either were not able to provide thermal conductivity in both directions or which resulted in the destruction of the sample.

A further object of the present invention is to provide a method of determining an anisotropic ratio for a sample, comprising the steps of:

providing a thermal probe for applying a voltage signal to the sample;

contacting the sample to be tested with the probe;

generating a first anisotropic thermal parameter for a plurality of directions on the sample simultaneously;

compiling the data for each direction; and calculating an anisotropic ratio for the sample.

By making use of a central processing unit, the thermal conductivity system can be fully automated with the gathering and manipulation of the data by the CPU. With the system according to one embodiment of the present invention, a thermal parameter, namely the $k\rho c_p$, of a material, where the k denotes thermal conductivity, $\rho$ denotes density and $c_p$ is the heat capacity of a material. The system permits testing within 30 seconds with high precision of the order of plus or minus 2 percent (±2%). A second test which may be achieved by making use of the system according to the present invention is used on oriented samples such as wood or machined polymers as indicated hereinabove generally, such samples have properties which differ depending on the orientation during testing and are therefor said to have anisotropic properties.

A still further object of the present invention is to provide a method of generating an anisotropic ratio for sample material having isotropic and anisotropic properties comprising the steps of:

providing a voltage detection means for detecting voltage fluctuations;

contacting the sample to be tested with the voltage detection means;

simultaneously detecting an isotropic thermal parameter and an anisotropic thermal parameter on the sample; and generating an anisotropic ratio from the isotropic thermal parameter and the anisotropic thermal parameter for the sample.

By practicing the method according to the present invention, a user may determine the thermal conductivity in a machine direction and a transverse direction in a simultaneous manner. This is particularly useful information and when combined with the speed of the test, it is clear that the method according to the present invention has substantial utility with respect to quality control and quality assurance for any type of material. In this regard, the present invention clearly circumvents the previous difficulties and limitations associated with existing arrangements in this field.

Having thus generally described the invention, reference will now be made to the accompanying drawings illustrating preferred embodiments.

BRIEF DESCRIPTION OF THE DRAWINGS

Similar numerals in the drawings denote similar elements.

DETAILED DESCRIPTION OF THE PREFERRED EMBODIMENTS

Figure 1:
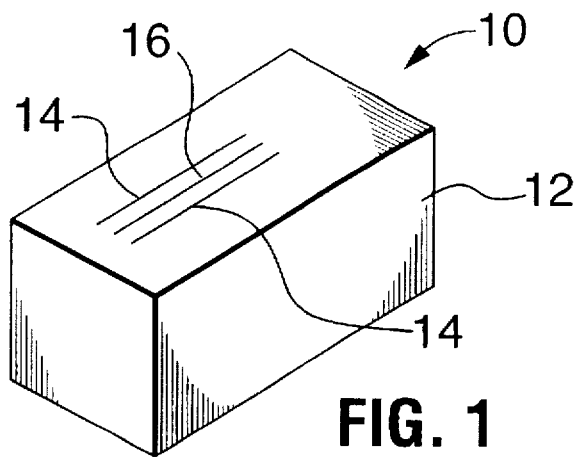
FIG. 1 is a perspective view of one embodiment of the probe according to the present invention.
Figure 2:
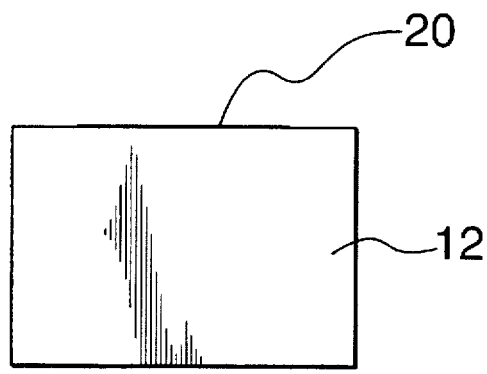
FIG. 2 is an end view of the embodiment of FIG. 1.
Figure 3:
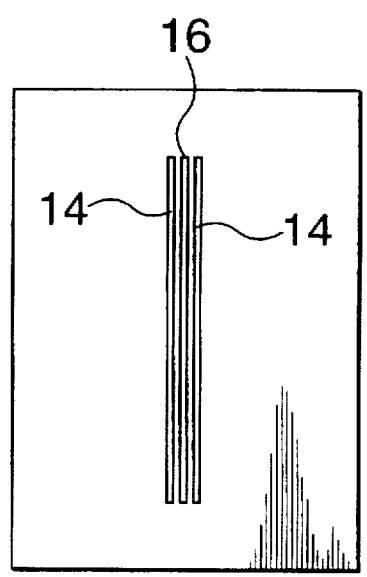
FIG. 3 is a bottom view of the embodiment of FIG. 1.
Figure 4:
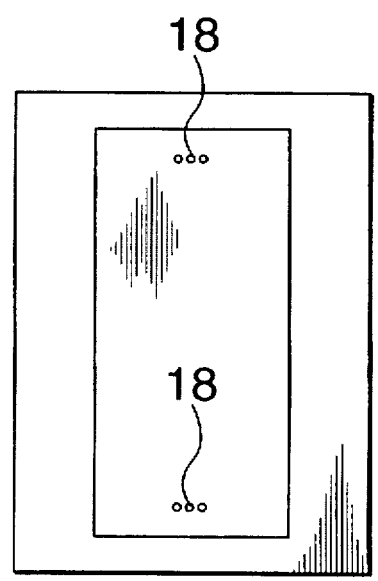
FIG. 4 is a top view of the embodiment illustrated in FIG. 1.

Referring now to FIGS. 1 through 4, shown is one example of a probe, globally denoted by numeral 10. The probe includes a non-electroconductive insulating body 12, shown in the example as a generally block-like structure. The body 12 may be any suitable insulating material, however, an advantageous embodiment employs polyurethane foam as the non-electroconductive material. In the embodiment shown in FIG. 1, two outer electroconductive members 14 flank a middle electroconductive member 16. The electroconductive members 14 and 16 comprise wire, ribbons etc. and in a preferred form, the members 14 and 16 comprise nickel wires. As will be appreciated by those skilled in the art, any suitable form for the electroconductive members be suitable, with the only proviso that the surface bearing the members 14 and 16 remain reasonably flat so as not to impede contact of the probe on the surface to be tested. Leads (not shown) extend through the body 12 and are in electrical communication with each of the members 14 and 16 at both ends thereof and terminate at solder points 18 as illustrated in FIG. 4. Metal plate 20 acts as a surface upon which the electroconductive members 14 and 16 can be attached to solder points 18.

Advantageously, members 14 and 16 are of a thin enough form to yield a sufficiently higher resistance to make it possible to record a voltage difference when the same are in contact with a sample. In addition, the lengths of the conductive members 14 and 16 are sufficiently long to cause heat flow in the longitudinal direction to be negligible. In the embodiment shown in FIG. 1, in a first possible testing procedure, the outer strips 14 may be heated to provide thermal guarding therefor reducing heat flow in the direction of these members. This feature provides a one-dimensional heat flow when the guard members 14 are activated during a first test and a two dimensional test when they are not activated.

Figure 5:
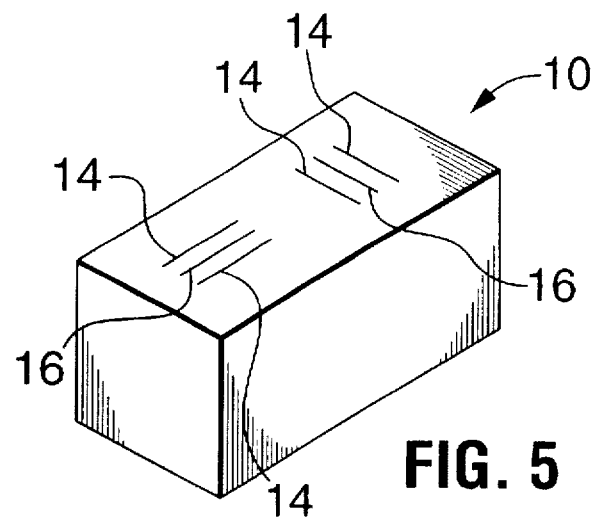
FIG. 5 is a perspective view of an alternate embodiment.

FIG. 5 shows an alternate embodiment of the present invention wherein electroconductive members are provided in a first direction suitable for testing in the machine direction of a sample and in a second direction suitable for sampling in the transverse direction.

Figure 6:
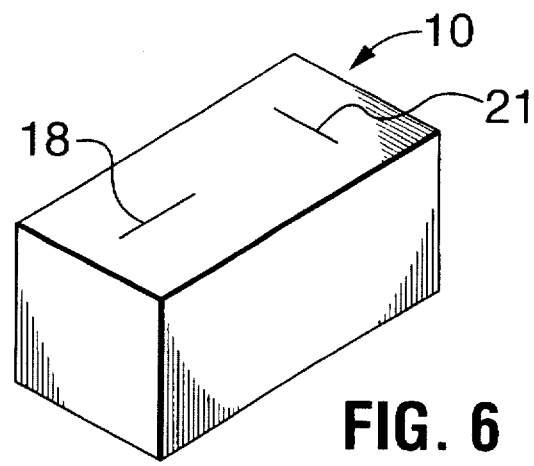
FIG. 6 is a perspective view of a further alternate embodiment.

Referring to FIG. 6, shown is a further embodiment of the present invention wherein there is only a single electroconductive member 18 and 21 for application to the machine direction and transverse direction respectively.

Figure 7:
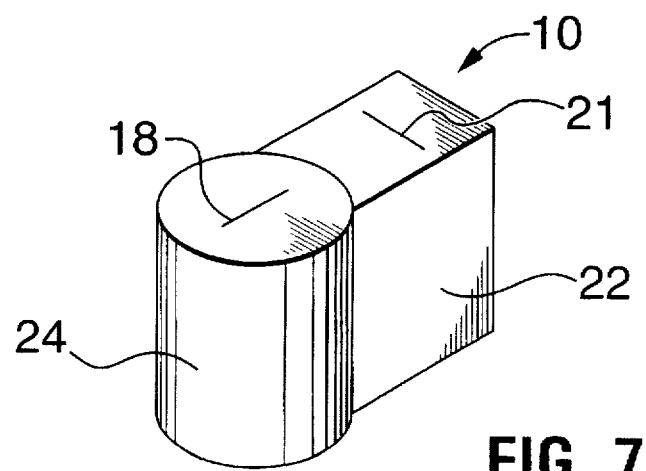
FIG. 7 is a perspective view of a still further alternate embodiment.

FIG. 7 shows a further embodiment, similar to FIG. 6, with the additional feature that body has been split into two members 22 and 24 with each of these members being movable relative to one another. In this embodiment, the angular relationship of members 18 and 21 can be varied from the orthogonal relationship. These members generally provide in previous embodiments and can be rotated such that the angle between them is variable.

Figure 8:
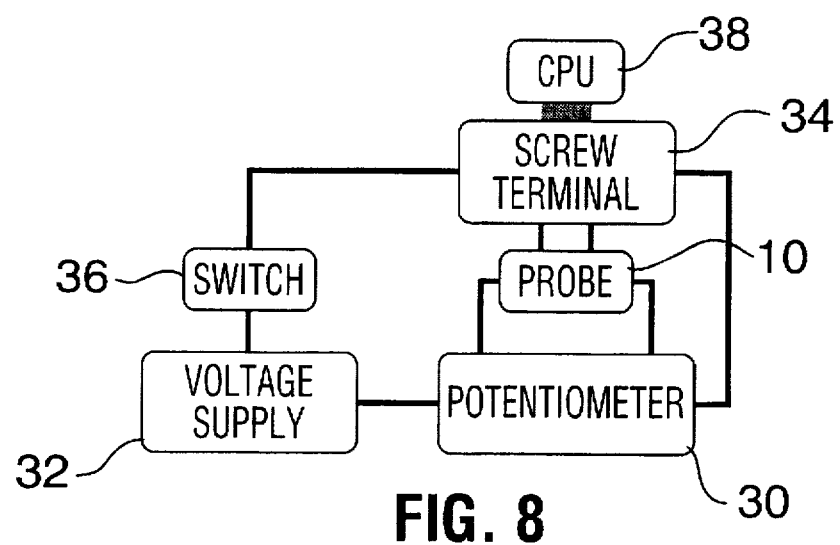
FIG. 8 is a block diagram illustrating the components in a thermal conductivity system employing the probe.
Figure 9:
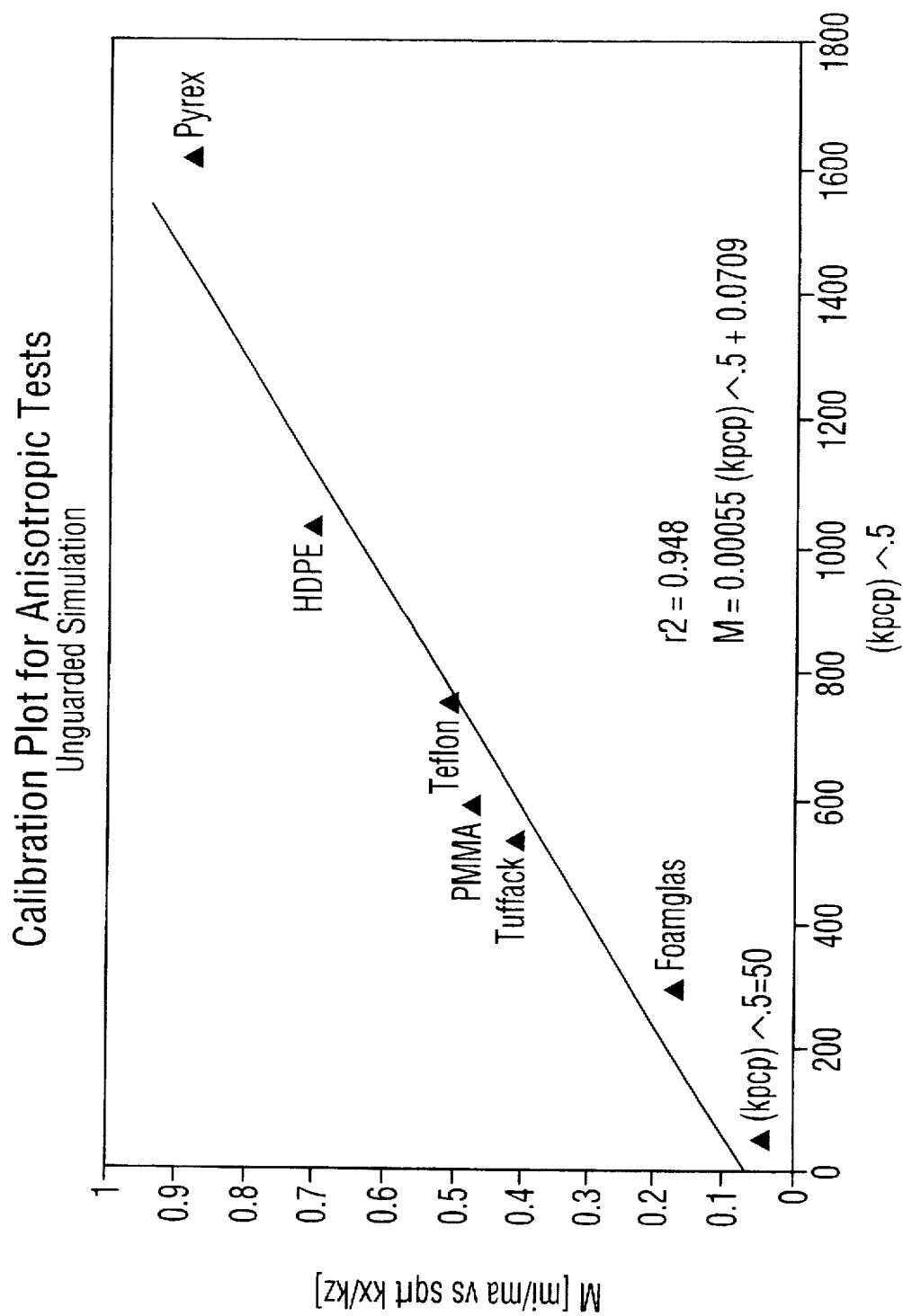
FIG. 9 is an anisotropic calibration graph.

Referring now to FIG. 8, shown is a block diagram of the components and their interrelation in the system for measuring thermal conductivity. In the drawing, probe 10 is connected to a resistor box 30, (potentiometer) the resistor box being in electrical communication with the conventional voltage supply 32 and a screw terminal 34. A switch 36 is provided intermediate the voltage supply 32 and the screw terminal 34. A CPU 38 receives the data from the screw terminal. A typical CPU suitable for use is a 386 IBM computer with a math co-processor and data acquisition board (DAS 8PGA). Data acquisition software provided programmable gain to allow monitoring of the voltage over different input ranges and produced an output voltage signal sufficient to activate switch 36. Generally speaking, the first test to be performed when measuring an anisotropic ratio is a guarded test on an isotropic cast sample of the oriented series to be studied. This determines the square root of $kpc_p$. This value is used in an equation to calculate M, a factor which relates to the level of sensitivity of a material to respond to anisotropy. From the value of M, B can be calculated. In order to calculate the anisotropic ratio of the sample, two tests are performed at 90° relative to one another, both having the same normal axis as the isotropic test referred to hereinabove. Once the tests are completed, the ratio of $V_o^3 m^{-1}$ axial to $V_o^3 m^{-1}$ transverse must be entered into a further equation from the calibration plot illustrated in FIG. 9 for an unguarded test to yield the value of $k^{axil}(k_{trans})^{-1}$, the anisotropy ratio. The tests are conducted at the same initial voltage.

As is known in this art, the term axial is synonymous with the machine direction. This is also true for the term "trans" which is understood in the art to relate to the transverse direction.

The temperature rise at the interface between the sample and the heating element is measured by using the heating element (the electroconductive member) as the thermocouple. The change in temperature results in a change in the resistance of the heating elements and if they are exposed to a constant current, the voltage changes in proportion to the temperature. The voltage changes are measured with a potentiometer in a manner well known to those skilled in this art. The changes in voltage comprise the difference between the initial voltage and the subsequent voltage and in this manner, the change is effectively the subsequently increased voltage.

Having thus described the invention, reference will now be made to the examples.

EXAMPLE 1

The unguarded procedure was difficult to calibrate as it was not possible to test series of well documented anisotropic samples. A numerical simulation was used to replace characterized samples. Simulations of tests were run on anisotropic series of samples with the same properties as the actual samples used for isotropic calibration. Anisotropy factors ran from one to fifty and as anisotropy increased the rise in temperature at the interface decreased. This led to a decrease in slope of delta voltage versus the square root of time. When a cross plot is taken of the square root of the anisotropy factor versus the ratio of the slopes, a linear line is generated that has a slope (M) and intercept (B) specific for the sample simulated.

A variety of samples were simulated as described above and the specific slopes (M) were plotted against the sample parameter $(kpc_p)^{1/2}$. This plot, FIG. 9, becomes the calibration plot of an anisotropic test. In order to use this plot, an isotropic sample in an anisotropic series must first be tested by the isotropic guarded method to determine $(kpc_p)^{1/2}$. This allows for the calculation outlined in equations 1, 2 and 3.

$$\frac{k_{axial}}{k_{trans}} = \left( \frac{\frac{V_o^3/m_{axial}}{V_o^3/m_{trans}} - B}{M} \right)^2 \quad (1)$$

$$B = 1 - M \quad (2)$$

$$M = 0.00055 \, (kpc_p)^{1/2} + 0.0709 \quad (3)$$

where:
M=dimensionless constant (originating from a slope)
B=dimensionless constant (originating from a y intercept)
$V_o^3/m$=experimental parameter of given orientation

EXAMPLE 2

As stated earlier, strength of an oriented sample is currently most commonly measured by taking a sample and destructively testing it. If it could be shown that a non-destructive thermal conductivity test yielded the same quantitative measure of strength, both time and money could be saved during polymer production.

Mergenthaler (stretched PE), Choy (roll/draw HDPE) and Saunders (roll/drawn PET) have found a linear relationship between thermal conductivity anisotropy and Young's Modulus. The plots (FIG. 10) show remarkable agreement with all curves having $r_2>0.973$. Choy's data must be qualified by noting that his second set of data represents thermal conductivities measured at 120 K.

Figure 10:
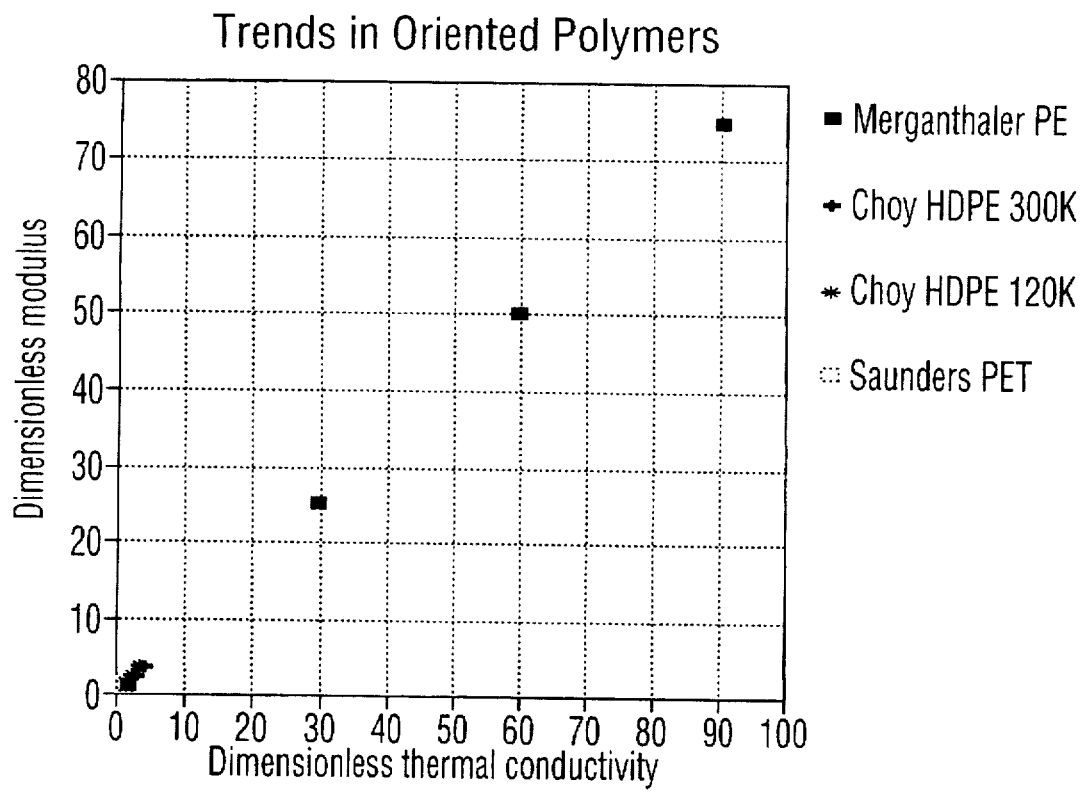
FIG. 10 is a plot of thermal conductivity anisotropic ratio versus strength in oriented polymers.

The x-axis found in FIG. 10, $k_a/k_{a1}$, is a dimensionless quantity to compare the axial thermal conductivity in an oriented sample to that of a baseline unoriented sample.

$$\frac{k_a}{k_{a1}} = \frac{\text{thermal conductivity}}{\text{thermal conductivity}_{initial}} \quad (4)$$

Mergenthaler's data shows a thermal conductivity ratio to be proportional to a strength ratio up to a Young's Modulus increase of a factor of 75. This occurs at a draw ratio of 40 and it is important to note that the graph is linear at this level of DR. This represents a high level of orientation for PE but Mergenthaler states that the K versus modulus trend still increases in the range of complete orientation. This gives more evidence for the same molecular mechanisms in both properties but thermal conductivity would provide a fast, non-destructive, on-line method of quality control.

EXAMPLE 3

Figure 11A:
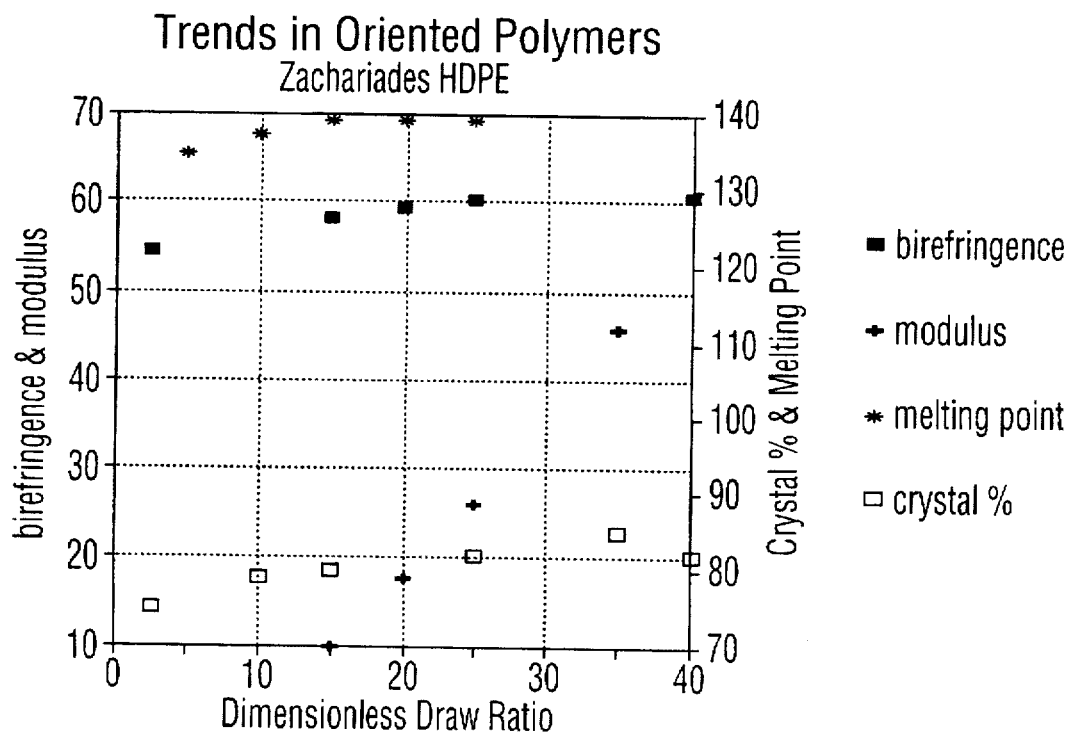
FIG. 11a is a plot of optical methods.

Zachariades and Saunders studied other properties as they relate to draw ratio. FIG. 11a shows that birefringence, crystal percentage and melting point of HDPE increase to a draw ratio of approximately 20 and then level off where modulus continues to increase linearly over the entire test region extending to a DR of 35. This suggests that the mechanisms differ for the increase in modulus.

Figure 11B:
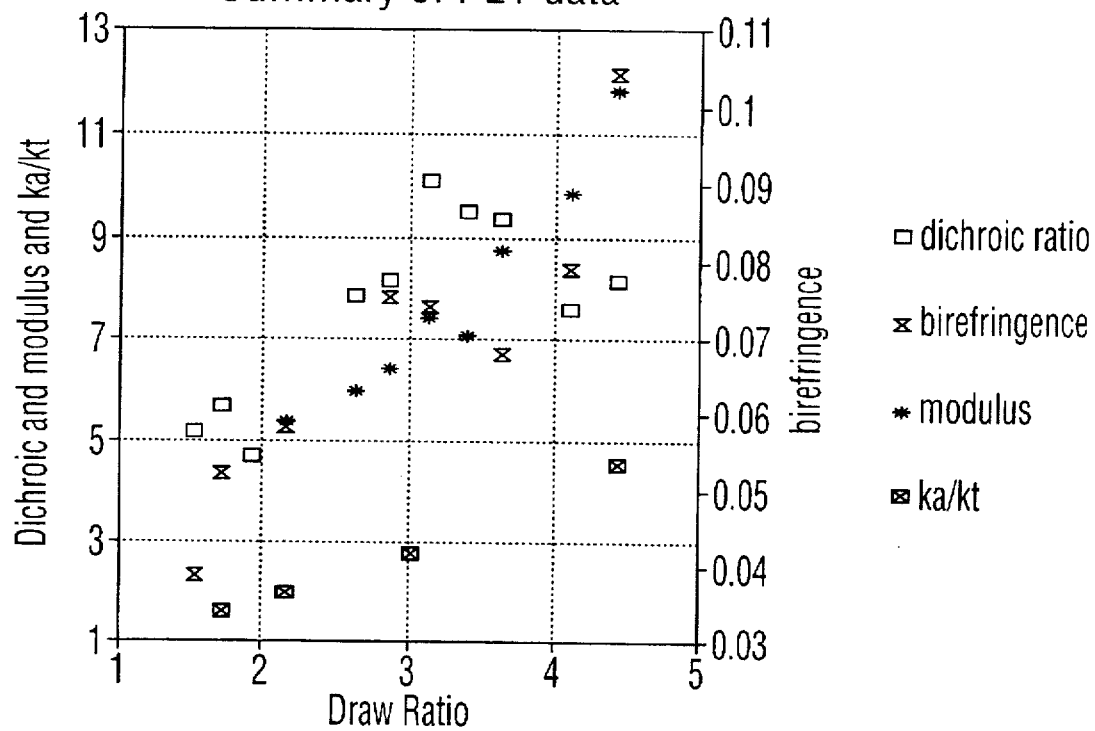
FIG. 11b is a plot of optical methods compared to thermal conductivity anisotropic ratio as a predictor of strength.

Saunders also studied other material properties such as dichroic ratio and birefringence as well as modulus and thermal conductivity anisotropy (FIG. 11b). The range of draw ratios is much lower, only going to DR of 4.45, but even over that range it can be seen that the modulus and ka/kt are linearly related to draw, where the other data is scattered and shows a plateau trend. This indicates that the same mechanisms may be responsible for the increase in modulus and ka/kt, this being the creation of tie molecules.

EXAMPLE 4

A series of roll-drawn polyethylene terephthalate (PET) was obtained from the National Research Council Industrial Material Institute (IMI) in Boucherville, Quebec. These samples were characterized with draw ratios up to 4.45 as well as infrared dichroism, modulus and birefringence measurements.

The samples were thin and therefor had to be cut and laminated together in order to have sufficient thickness to cover the three wires of the probe. The surfaces to be tested were machined to provide proper surface contact. First the samples were tested without the use of the unguarded calculation procedure. One dimensional tests were performed on the normal, transverse and machine faces to obtain values for $kpc_p$, which then was used to calculate the anisotropy ratio ka/kt. A plot of this ratio as a function of draw ratio follows in FIG. 12. The plot shows a linear increase in anisotropy with draw ratio.

Figure 12:
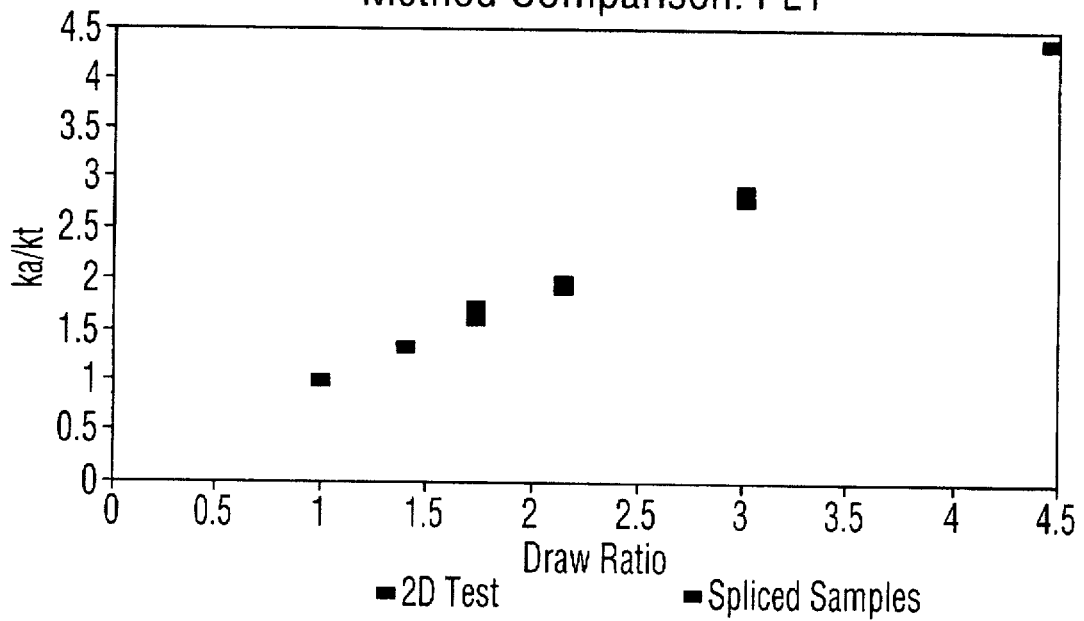
FIG. 12 is a comparative plot of two methods of evaluating thermal conductivity anisotropic ratio.

The same series of samples was tested with the unguarded method for anisotropic samples and the results are included on FIG. 12 showing the comparison to be excellent between the two techniques. The unguarded method was non-destructive except for the machining of the sample on one side, and therefor is preferred over the splicing method described. Also, the unguarded method could be accomplished without moving the sample, where the splicing method required the sample to be moved in order to test the three different orientations.

Having described preferred embodiments to the present invention, it will be understood that various modifications or alterations can be made to the above-described embodiments without departing from the spirit and scope of the present invention.

I claim:

1. A method for determining a thermal conductivity ratio of a sample in both a machine direction and a transverse direction, comprising the steps of:

providing a measuring device having a flat surface with at least one electroconductive member in a transverse direction and at least one electroconductive member in a machine direction;

applying a steady current at an initial voltage through said at least one electroconductive member in each direction to elevate the temperature of each of said electroconductive members in each direction in the absence of thermal guarding;

contacting, at a selected flat surface on said sample, each of said electro conductive members in each direction;

determining an amount of voltage change from said initial voltage by each of said electroconductive members for both said transverse direction and said machine direction; and combining the voltage changes to generate a thermal conductivity ratio from the determined voltage changes for said machine direction and said transverse direction.

2. The method as set forth in claim 1, wherein the voltage changes are detected with a potentiometer.

3. The method as set forth in claim 1, wherein said method is non-intrusive.

4. The method as set forth in claim 1, wherein said method is non-destructive.

5. The method as set forth in claim 1, wherein said measuring device includes at least three electroconductive members in a spaced apart relationship in a transverse direction and at least three spaced apart electroconductive members in a machine direction, said transverse direction and said machine direction being in an orthogonal relationship.

* * * * *